United States Patent
Joo et al.

(10) Patent No.: US 10,004,637 B2
(45) Date of Patent: Jun. 26, 2018

(54) ANTERIOR CAPSULOTOMY GUIDE DEVICE FOR CATARACT SURGERY

(71) Applicants: Catholic University Industry Academic Cooperation Foundation, Seoul (KR); Lucid Korea Co., Ltd., Gyeongsangbuk-do (KR)

(72) Inventors: Choun-Ki Joo, Seoul (KR); Dong Jin Chang, Seoul (KR); Chong Houn Lee, Seoul (KR); Dong Kun Lee, Gyeonggi-do (KR)

(73) Assignees: Catholic University Industry Academic Cooperation Foundation, Seoul (KR); Lucid Korea Co., Ltd., Gyeongsangbuk-do (KR)

( * ) Notice: Subject to any disclaimer, the term of this patent is extended or adjusted under 35 U.S.C. 154(b) by 136 days.

(21) Appl. No.: 14/436,115

(22) PCT Filed: Oct. 18, 2013

(86) PCT No.: PCT/KR2013/009316
§ 371 (c)(1),
(2) Date: Apr. 16, 2015

(87) PCT Pub. No.: WO2014/062024
PCT Pub. Date: Apr. 24, 2014

(65) Prior Publication Data
US 2015/0305934 A1    Oct. 29, 2015

(30) Foreign Application Priority Data
Oct. 19, 2012    (KR) .................. 10-2012-0116676

(51) Int. Cl.
*A61F 9/007*    (2006.01)

(52) U.S. Cl.
CPC .................. *A61F 9/00736* (2013.01)

(58) Field of Classification Search
CPC ... A61F 9/00736; A61F 9/00754; A61F 2/147
See application file for complete search history.

(56) References Cited

U.S. PATENT DOCUMENTS

| 4,452,235 A | * | 6/1984 | Reynolds | A61F 2/147 |
| | | | | 128/898 |
| 5,098,443 A | * | 3/1992 | Parel | A61F 2/14 |
| | | | | 128/898 |

(Continued)

FOREIGN PATENT DOCUMENTS

| JP | 2000-237218 A | 9/2000 |
| JP | 2012-515017 A | 7/2012 |

(Continued)

OTHER PUBLICATIONS

China Patent Office, Office Action dated Dec. 2, 2015 against corresponding Chinese Patent Application No. 201380054783.5 with an English translation.

*Primary Examiner* — Alexander Orkin
(74) *Attorney, Agent, or Firm* — Hammer & Associates, P.C.

(57) ABSTRACT

The present invention relates to an anterior capsulotomy guide device for cataract surgery. The present invention relates to an anterior capsulotomy guide device for cataract surgery which is temporarily inserted for anterior capsulotomy during cataract surgery, wherein the anterior capsulotomy guide device comprises a ring-shaped body, and a cut portion is formed by cutting a part of the body. According to the present invention, it is possible to carry out anterior capsulotomy with precise size and shape during cataract surgery, thereby maximizing the effect of cataract surgery.

4 Claims, 1 Drawing Sheet

(56) References Cited

U.S. PATENT DOCUMENTS

| | | | | |
|---|---|---|---|---|
| 5,300,118 A | * | 4/1994 | Silvestrini | A61F 2/147 606/166 |
| 5,323,788 A | * | 6/1994 | Silvestrini | A61F 9/0133 128/897 |
| 5,505,722 A | * | 4/1996 | Kilmer | A61F 2/147 606/1 |
| 5,676,669 A | * | 10/1997 | Colvard | A61F 9/00736 606/107 |
| 8,157,797 B2 | | 4/2012 | Boukhny et al. | |
| 2001/0004708 A1 | | 6/2001 | Nagai | |
| 2006/0149194 A1 | * | 7/2006 | Conston | A61B 17/32002 604/294 |
| 2010/0312252 A1 | * | 12/2010 | Jia | A61B 18/10 606/107 |
| 2013/0253402 A1 | * | 9/2013 | Badawi | A61F 9/0017 604/8 |

FOREIGN PATENT DOCUMENTS

| | | |
|---|---|---|
| KR | 10-2000-0066014 A | 11/2000 |
| KR | 10-1039398 B1 | 6/2011 |
| KR | 10-2011-0084887 | 7/2011 |

* cited by examiner

[Fig. 1]
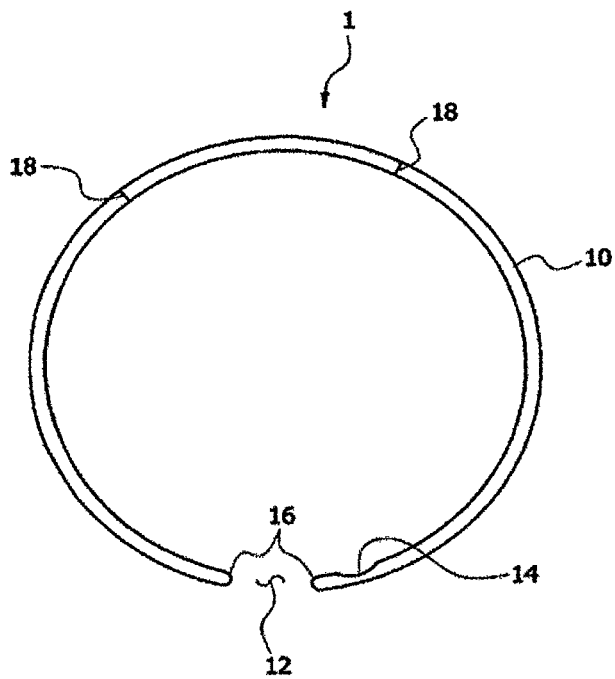
[Fig. 2]
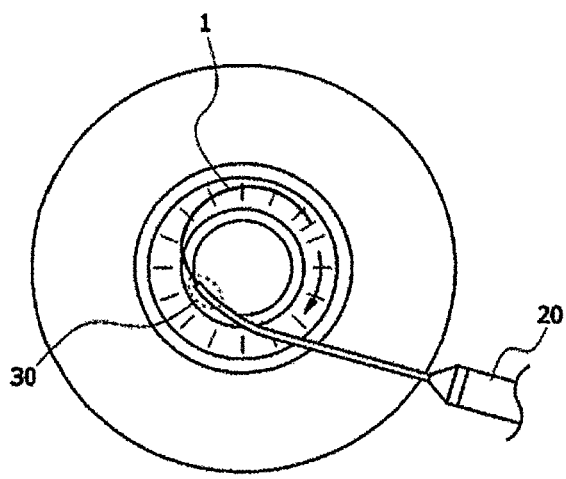

ANTERIOR CAPSULOTOMY GUIDE DEVICE FOR CATARACT SURGERY

TECHNICAL FIELD

The present invention relates to an anterior capsulotomy guide device for cataract surgery, and more particularly, to an anterior capsulotomy guide device for cataract surgery which is inserted to carry out anterior capsulotomy with precise shape and size during cataract surgery.

BACKGROUND ART

A crystalline lens surgically and anatomically includes an anterior capsule, a cortex, a nucleus, and a posterior capsule, but a cataract clouds these constituent elements. The cataract is an adult disease that rapidly increases in persons over the age of 60, and significantly increases in progression and degree of clouding, and the cataract is the most common disease as the reason of blindness.

Regarding the treatment of the cataract, there is only a surgical method of removing the crystalline lens with the clouding, and inserting an artificial transparent crystalline lens, which is made artificially, onto the location from which the crystalline lens has been removed. At present, a surgical method, which is most widely used for cataract surgery, is a surgical method of inserting the artificial crystalline lens into the capsule after phacoemulsification, and the procedure thereof is widely carried out in the sequence of keratotomy, anterior capsulotomy, phacoemulsification and aspiration, decortication, and insertion of the artificial crystalline lens.

The perfectly circular anterior capsulotomy has the following meanings in the cataract surgery.

First, when the anterior capsule is removed as a single piece, the anterior capsule does not become an obstacle and does not hinder a subsequent surgical operation.

Second, force, which is transferred to the capsule during the surgical operation, is uniformly distributed to disperse force that is transferred to a ligament of the crystalline lens, thereby preventing dislocation of the crystalline lens during and after the surgical operation.

Third, the circular anterior capsulotomy allows the eye to have a stable close system, thereby preventing damage to the posterior capsule.

Fourth, the circular anterior capsulotomy increases physical stability while manipulating the capsule during a surgical operation (separation of nucleus, nucleus splitting, a manipulation of the crystalline lens, and the like), thereby reducing surgical complications.

Fifth, by preventing shrinking and clouding of the capsule after the surgical operation, it is possible to prevent a deterioration in eyesight that may occur again after a successful surgical operation.

In addition to the circular shape, the size is also an important factor that determines success and failure during the anterior capsulotomy. In general, the size of the capsulotomy is slightly smaller than a size of an optical unit of the artificial crystalline lens. If the size of the capsulotomy is greater than the size of the optical unit of the artificial crystalline lens, there may occur dislocation of the artificial crystalline lens, iridentropium, deviation, and the like which may cause a deterioration in eyesight, and in a serious case, reoperation may be carried out. In addition, if the size of the capsulotomy is excessively small, shrinking of the capsule occurs, which blocks a visual axis and causes a deterioration in eyesight and causes clouding of the anterior capsule and the posterior capsule, and whereby an additional surgical operation is required, and the shrinking of the capsule causes dislocation of the artificial crystalline lens, which may cause a deterioration in quality of eyesight after the surgical operation. Korean Patent Application Laid-Open No. 2011-0084887 discloses a cystitomy device.

Recently, the importance of the anterior capsulotomy with a perfectly circular and appropriate size is further increased as use of multifocal artificial crystalline lenses for correcting presbyopia and use of artificial crystalline lenses for correcting astigmatism are increased. In the case of the artificial crystalline lens, the complications after a surgical operation, such as abnormality in position, or clouding of the posterior capsule, have a greater effect on eyesight than a short focal length artificial crystalline lens, and an additional manipulation itself for solving the complications may cause a deterioration in performance of the artificial crystalline lens.

Surgeons with much experience usually perform the anterior capsulotomy based on a size of a cornea of a patient and a size of an enlarged pupil. However, the size of the cornea differs from patient to patient, and the size of the enlarged pupil is also not uniform, such that a final size is not uniform. Because the shape of the anterior capsulotomy depends only on the experience and the surgical technique of the surgeon, it is very difficult to perform the perfectly circular anterior capsulotomy. In addition, if the size and the shape of the anterior capsulotomy are not perfect, an additional surgical operation needs to be carried out in order to adjust the size of the capsule of the crystalline lens after inserting the artificial crystalline lens, which causes a waste of time and efforts.

As described above, because the anterior capsulotomy is a very precise surgical operation, there is a need for a device capable of guiding a precise size and a position during the anterior capsulotomy.

DISCLOSURE

Technical Problem

Therefore, an object of the present invention is to solve the aforementioned problem in the related art, and to provide an anterior capsulotomy guide device for cataract surgery, which guides the anterior capsulotomy to be carried out with a precise shape and size during the cataract surgery.

Technical problems to be solved by the present invention are not limited to the aforementioned technical problem, and other technical problems, which are not mentioned above, may be clearly understood from the following descriptions by those skilled in the art to which the present invention pertains.

Technical Solution

In order to achieve the aforementioned object, according to one exemplary embodiment of the present invention, the present invention provides an anterior capsulotomy guide device for cataract surgery which is temporarily inserted for anterior capsulotomy during the cataract surgery, the anterior capsulotomy guide device including: a ring-shaped body, in which a cut portion is formed by cutting a part of the body.

According to another exemplary embodiment of the present invention, the present invention provides an anterior capsulotomy guide device for cataract surgery which is temporarily inserted for anterior capsulotomy during the cataract surgery, the anterior capsulotomy guide device including: a ring-shaped body, in which the body is formed as an open loop having a part that is cut.

Advantageous Effects

In the present invention, the cataract surgery is carried out by using the elastically deformable guide device having an open loop shape, such that it is possible to carry out the anterior capsulotomy with precise size and shape during the cataract surgery, thereby maximizing the effect of the cataract surgery.

DESCRIPTION OF DRAWINGS

FIG. 1 is a view illustrating an anterior capsulotomy guide device for cataract surgery according to an exemplary embodiment of the present invention.

FIG. 2 is a view exemplarily illustrating a state in which the anterior capsulotomy guide device is inserted according to an exemplary embodiment of the present invention.

DESCRIPTION OF MAIN REFERENCE NUMERALS OF DRAWINGS

1: Anterior capsulotomy guide device
10: Body
12: Cut portion
14: Fastening groove
16: End
18: Grip portion
20: Insertion tool
30: Corneal incision Best Mode According to an exemplary embodiment of the present invention, the present invention provides an anterior capsulotomy guide device for cataract surgery which is temporarily inserted for anterior capsulotomy during the cataract surgery, the anterior capsulotomy guide device including: a ring-shaped body, in which a cut portion is formed by cutting a part of the body.

A fastening groove may be formed at an end of the body which is formed with the cut portion.

The end of the body, which is formed with the cut portion, may be formed as a curved surface.

At least one or more grip portions, which is gripped by using a tool, may be defined at the body.

The body may be made of an elastically deformable material.

The body may be made of a polymeric material.

A surface of the body may be coated with a luminous material.

The body may have a diameter of 5.5 mm to 6.0 mm.

According to another exemplary embodiment of the present invention, the present invention provides an anterior capsulotomy guide device for cataract surgery which is temporarily inserted for anterior capsulotomy during the cataract surgery, the anterior capsulotomy guide device including: a ring-shaped body, in which the body is formed as an open loop having a part that is cut.

Mode for Invention

Hereinafter, an exemplary embodiment of an anterior capsulotomy guide device for cataract surgery according to the present invention will be described in detail with reference to the accompanying drawings.

FIG. 1 is a view illustrating an anterior capsulotomy guide device for cataract surgery according to an exemplary embodiment of the present invention.

As illustrated in FIG. 1, an anterior capsulotomy guide device 1 according to the present invention is a device which is temporarily inserted for anterior capsulotomy during cataract surgery, and in the present exemplary embodiment, the anterior capsulotomy guide device 1 serves to allow the anterior capsulotomy to be carried out with a precise shape and size during the cataract surgery.

The anterior capsulotomy guide device includes a ring-shaped body 10. The body 10 is formed in a ring shape having a predetermined thickness, and for example, may be made of an elastically deformable material such as a polymeric material so as to be smoothly inserted into an corneal incision 30 (see FIG. 2) for the anterior capsulotomy. That is to say, the body 10 is elastically deformed when the body 10 is being inserted into the corneal incision 30, and then, the body 10 is restored to the original state and maintains the shape thereof after the body 10 is inserted into the corneal incision 30.

Further, a cut portion 12 is formed by cutting a part of the body 10. That is, the cut portion 12 is formed at a part of the ring-shaped body 10, such that an open loop is formed instead of a closed loop. In the present exemplary embodiment, the reason why the body 10 is formed as an open loop is to more smoothly insert the body 10 into the corneal incision 30.

Specifically, ends 16 of the body 10 are formed at both sides of the cut portion 12, respectively. Therefore, one end 16 of the two ends 16 may be inserted first through the corneal incision 30, and then the body 10 may be inserted while being rotated to be in line with the corneal incision 30. The corneal incision 30 is not formed to be wide enough to accommodate the body 10 at one time, and as a result, the body 10 is configured with the aforementioned shape.

In addition, the end 16 of the body 10 may be formed as a curved surface so as to prevent an eyeball from being damaged in a state in which the end 16 of the body 10 is inserted into the corneal incision 30.

Meanwhile, a fastening groove 14 may be formed at the end 16 of the body 10. The fastening groove 14 is a portion that is formed to fasten a tool (not illustrated) when the body 10 is removed from the corneal incision 30 after the body 10 is inserted into the corneal incision 30. The fastening groove 14 may be formed at both the ends 16 or only at any one of the two ends 16.

In addition, a grip portion 18, which is gripped by using a tool (not illustrated) such as a pincer when the body 10 is inserted into the corneal incision 30, may be formed at one side of the body 10. At least one or more grip portions 18 may be formed, and may be formed at the opposite side to the portions where the ends 16 are formed.

The aforementioned body 10 has a ring shape, such that the body 10 may be restored to the original shape while being elastically deformed even after the body 10 is inserted into the corneal incision 30, thereby exhibiting an excellent surgical operation result during the anterior capsulotomy. In addition, a size of the body 10 is slightly smaller than a size of an optical unit of an artificial crystalline lens, and for reference, the optical unit of the artificial crystalline lens may be sized to have various diameters of 6.0 mm, 5.5 mm, etc. Therefore, the body 10 has a diameter of 5.0 mm to 6.0 mm, preferably, a diameter of 5.5 mm to 6.0 mm.

In addition, in the present exemplary embodiment, a surface of the body 10 may be coated with a luminous material such as a fluorescent material so that the body 10 may be easily discriminated when the body 10 is inserted and removed. In addition, the body 10 may be made of a material having a color for easily discriminating the body 10.

Hereinafter, a process of guiding the anterior capsulotomy by using the anterior capsulotomy guide device for cataract surgery according to the present invention, which has the aforementioned configurations, will be described in detail.

FIG. 2 is a view exemplarily illustrating a state in which the anterior capsulotomy guide device is inserted according to an exemplary embodiment of the present invention.

As illustrated in FIG. 2, the cut portion 12 is formed at one side of the body 10 that constitutes the anterior capsulotomy guide device 1. Therefore, as illustrated in FIG. 2, the surgeon first fixes the body 10 to a separate insertion tool 20. For example, the insertion tool 20 is formed in a hollow shape having a vacant space, and the elastically deformable body 10 is positioned in the insertion tool 20 while being elastically deformed.

In this case, the anterior capsulotomy guide device 1 is inserted through the corneal incision 30. In this process, when the body 10 exits from the insertion tool 20, the body 10 is elastically restored, and then may be restored to the original circular shape as illustrated in FIG. 2.

As such, when the body 10 is inserted into the corneal incision 30 and then restored to the original state, the body 10 maintains the circular shape, and when the guide device 1 maintains the circular shape, a probability that an excellent operation result will be exhibited is increased. In addition, when the body 10 is removed after the anterior capsulotomy, a separate tool is fastened to the fastening groove 14, thereby easily removing the body 10.

It is apparent that the scope of the present invention is not limited to the aforementioned exemplary embodiment but defined by the claims, and various modification and alterations may be made by those skilled in the art to which the present invention pertains without departing from the scope disclosed in the claims.

INDUSTRIAL APPLICABILITY

The anterior capsulotomy guide device according to the present invention may be effectively utilized for a surgical operation such as cataract surgery.

The invention claimed is:

1. A guide device for anterior capsulotomy which is temporarily inserted into an anterior capsule through a corneal incision during cataract surgery comprising:
   an insertion tool for the cataract surgery comprising a ring-shaped body, the body is formed as an open loop that controls a size of the corneal incision and a position of the anterior capsule, has a cut portion, is made of an elastically deformable material to allow the ring shape body to be inserted through and exit from the insertion tool, and has a diameter of 5.5 mm to 6.0 mm,
   a surface of the body is coated with a luminous material, and
   a fastening groove is formed at an end of the body which has the cut portion wherein a tool grips the body at the fastening groove as the body is removed from the corneal incision.

2. The guide device of claim 1 wherein the end of the body has a curved surface.

3. The guide device of claim 1 wherein at least one or more grip portions, which is gripped by using the tool, is defined at the body.

4. The guide device of claim 1 wherein the body is made of a polymeric material.

* * * * *